United States Patent [19]
Yamanaka et al.

[11] Patent Number: 6,078,353
[45] Date of Patent: Jun. 20, 2000

[54] ALL-PIXELS READING TYPE ELECTRONIC ENDOSCOPE APPARATUS

[75] Inventors: Kazuhiro Yamanaka; Mitsuru Higuchi, both of Omiya, Japan

[73] Assignee: Fuji Photo Optical Co., Ltd., Saitama, Japan

[21] Appl. No.: 08/927,184

[22] Filed: Sep. 11, 1997

[30] Foreign Application Priority Data

Sep. 12, 1996 [JP] Japan ................................. 8-263477
Sep. 17, 1996 [JP] Japan ................................. 8-267924

[51] Int. Cl.[7] ................................................. H04N 7/18
[52] U.S. Cl. ........................ 348/65; 358/435; 358/400; 358/401; 358/75; 358/450; 358/409; 379/100
[58] Field of Search .............................. 348/65, 68, 69, 348/70, 220, 257, 71, 66, 273; 379/100

[56] References Cited

U.S. PATENT DOCUMENTS

| | | | |
|---|---|---|---|
| 5,374,965 | 12/1994 | Kanno | 348/705 |
| 5,604,530 | 2/1997 | Saito et al. | 348/70 |
| 5,617,136 | 4/1997 | Iso et al. | 348/71 |
| 5,812,187 | 9/1998 | Watanabe | 348/70 |
| 5,929,900 | 7/1999 | Yamanaka et al. | 348/65 |
| 6,002,425 | 12/1999 | Yamanaka et al. | 348/68 |

Primary Examiner—Chris S. Kelley
Assistant Examiner—Shawn S. An
Attorney, Agent, or Firm—Snider & Associates; Ronald R. Snider

[57] ABSTRACT

An all-pixels reading type electronic endoscope apparatus enables the function of controlling the quantity of light which becomes impossible of follow-up when a still picture having a good picture quality is displayed to be quickly restored by reading all the pixels. The data on all the pixels obtained by a CCD at one exposure are read while using a light chopper, and the data on the odd lines are stored in a first memory and the data on the even lines are stored in a second memory. These memories are inhibited from being written into at the point of time when they store the picture data obtained at the same exposure, and the field signals formed from the video signals are stored in third and fourth memories. When a still picture is displayed, the third and fourth memories are inhibited from being written into, while the first and second memories are released from the write-inhibit state. It is thus possible to quickly restore the light quantity control function by inputting the current luminance signal to an iris controller before the display of the still picture is stopped. In addition, if the shutter speed is raised when the stop of the light source is not in a full-open state, and the shutter speed is lowered when the stop is in a full-open state, it is possible to obtain a picture having a higher quality.

1 Claim, 9 Drawing Sheets

FIG. 2
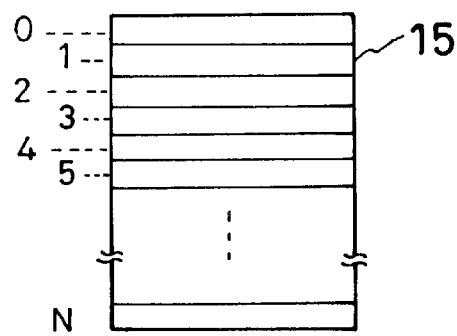
(A)
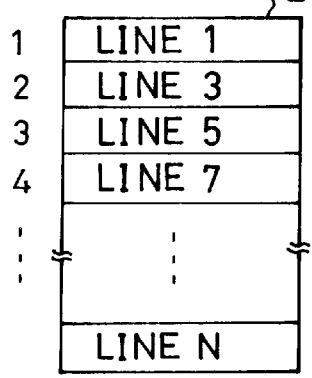
(B)
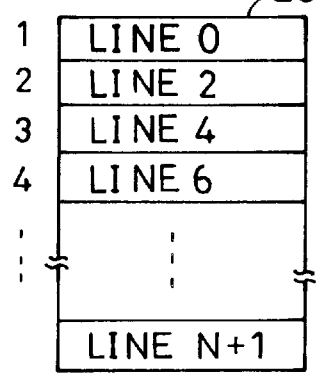
(C)
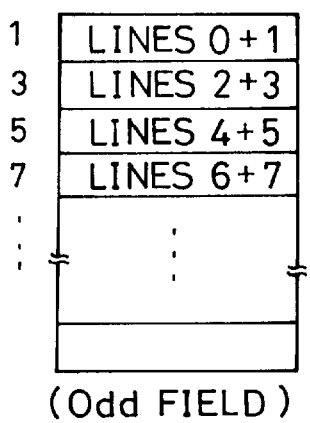
(Odd FIELD)
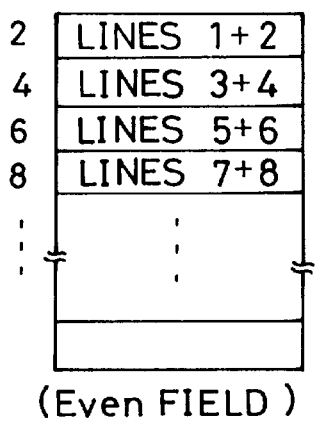
(Even FIELD)

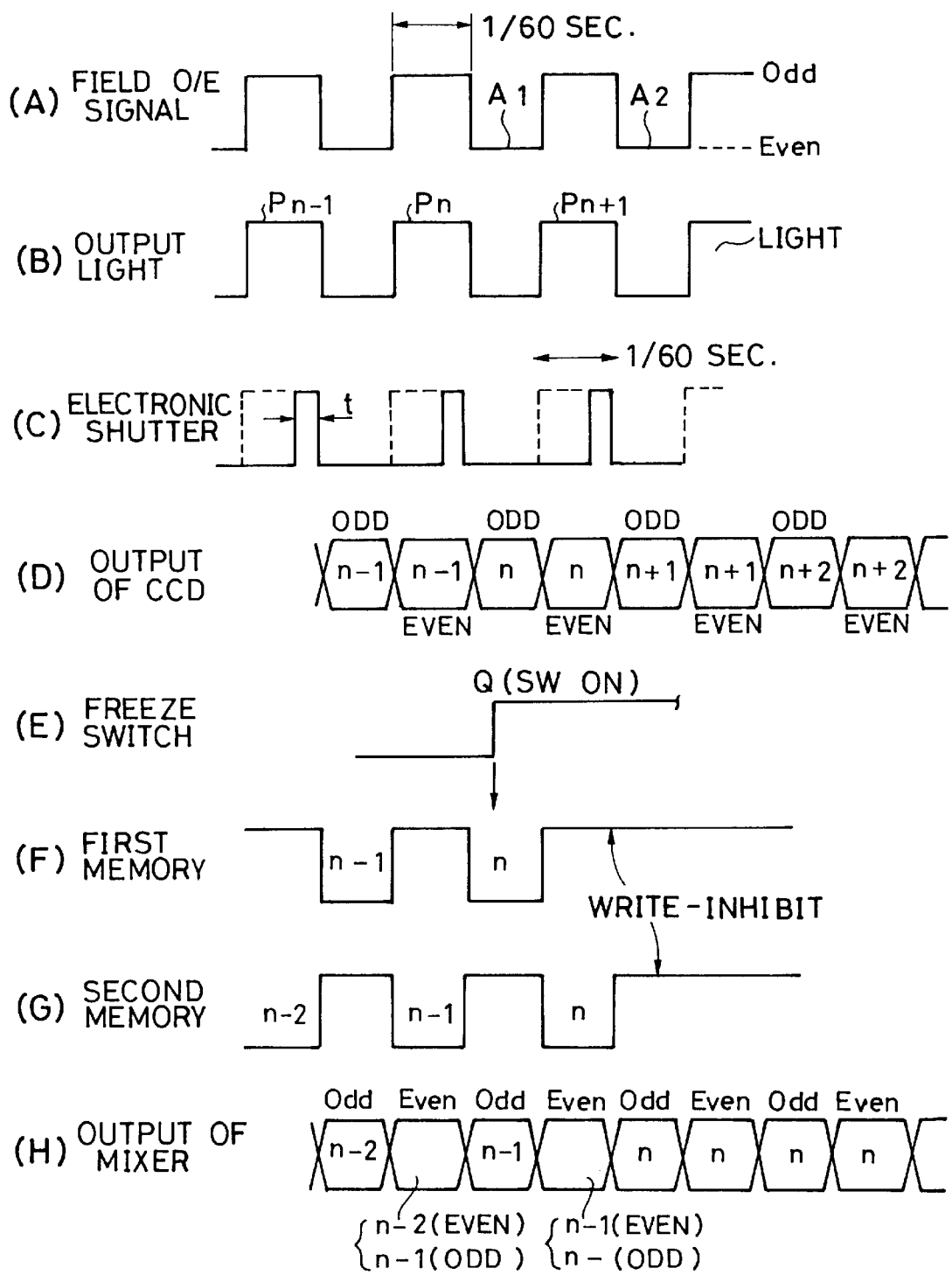

ALL-PIXELS READING TYPE ELECTRONIC ENDOSCOPE APPARATUS

BACKGROUND OF THE INVENTION

This application claims the priority of Japanese Patent Application No. 8-263477 filed on Sep. 12, 1996 and No. 8-267924 filed on Sep. 17, 1996 which are incorporated herein by reference.

1. Field of the Invention

The present invention relates to an all-pixels reading type electronic endoscope apparatus and, more particularly, to an all-pixels reading type electronic endoscope apparatus which reads all the pixels stored by an image sensor and which can adjust the quantity of light irradiated onto the object of observation to an appropriate value.

2. Description of the Related Art

In a CCD (Charge Coupled Device) which is an image sensor of an electronic endoscope, a video signal is obtained by reading an electric charge stored for each pixel by a photoelectric transducer. In a simultaneous electronic endoscope, a color filter for each pixel is disposed on the upper surface of the CCD so as to produce a color picture.

FIG. 10A shows the arrangement of color filters. As shown in FIG. 10A, for example, Mg (magenta), G (green), Cy (cyan) and Ye (yellow) filters are disposed for the respective pixels on the imaging surface of a CCD 1. Therefore, the CCD 1 obtains stored electric charges from the light which passes such color filters.

FIG. 10B shows the signals read by a conventional color difference line-sequential pixel mixture signal reading method. In this method, the stored electric charges of the pixels in a pair of horizontal lines are output in the form of a mixture. For example, at a first exposure, the video signals on lines 0 and 1, the video signals on lines 2 and 3, . . . in the odd (Odd) field are read out in the form of respective pixel mixture signals, and at a second exposure, the video signals on lines 1 and 2, the video signals on lines 3 and 4, . . . in the even (Even) field are read out in the form of respective pixel mixture signals. Therefore, a pixel mixture signal on two lines in the CCD 1 constitutes a signal on one line in a field picture.

FIG. 11 shows the signal reading operation in the CCD 1. An odd field and an even field are formed at intervals of 1/60 sec. (vertical synchronization period) as shown in a field O/E signal (A). Therefore, signals are stored at a storage (exposure) time t of an electron shutter (B), for example, and the signals are read out in the form of a pixel mixture signal in the next period of 1/60 sec.

As a result, (n−1) Odd field signals and n Even field signals are obtained, as shown in the read signal (C). The (n−1) Odd field signals are composed of the pixel mixture signals on lines (0+1), (2+3), (4+5) . . . , which are shown on the left side in FIG. 10(B) and the n Even field signals are composed of the pixel mixture signals on line (1+2), (3+4) . . . , which are shown on the right side in FIG. 10(B). By the interlaced scanning of the Odd field signals and the Even field signals, a picture for one frame is produced and displayed on a monitor.

In the above-described simultaneous electronic endoscope apparatus, however, since there is a time lag of 1/60 sec. when an odd field picture and an even field picture which constitute a picture for one frame are output one after another, if the endoscope itself or the object of observation moves during this 1/60 sec., the picture quality is deteriorated. Especially inconveniently, the picture quality is also deteriorated in a still picture displayed by the operation of a freeze button so as to enable detailed observation of a specified part.

According to the function of the electronic shutter of an electronic endoscope, it is possible to shorten the storage time in a light place so as to improve the picture quality. However, since there is a time lag of 1/60 sec. between the two storage times (exposures) for producing a picture for one frame, as shown in (B) of FIG. 11, the effect of the shortening of the storage time is not always gained.

A light source device of an electronic endoscope is provided with an iris controller for controlling the quantity of irradiated light to an appropriate value. However, when a still picture is displayed, the iris controller does not work for that period. The iris controller generally inputs a luminance signal which is formed from video signals and adjusts the stop so that the luminance signal has a predetermined value. When a still picture is displayed, the quantity of light is controlled on the basis of the luminance signal of the video signals for the still picture.

For this reason, the quantity of light is controlled on the basis of the past data at the point of time when the freeze switch is operated. If the end portion of the endoscope is moved during the display of the still picture and the distance between the end portion of the endoscope and the object of observation is changed, halation is caused or the screen becomes dark when the still picture is changed over to a moving picture. If the quantity of irradiated light is unnecessarily large, the part of observation sometimes gets burned during long-term observation.

In an electronic endoscope apparatus, when a function of adjusting the quantity of light is used, the storage time (shutter speed) is fixed at a predetermined value. On the other hand, when the electronic shutter function is used, the stop is fixed at a predetermined value. However, the function of adjusting the quantity of light is advantageous in that the light output from the light source is made variable, while the electronic shutter function is advantageous in that a sharp picture is obtained with a high shutter speed and in that a good picture quality is obtained even if the endoscope itself or the object of observation moves. Consequently, it is desirable to use the advantages of both functions at the time of taking an image. Especially, in an electronic endoscope device which can display a still picture for the purpose of detailed observation of a specified part, if it is possible to produce a good still picture even if the endoscope itself or the object of observation moves, the endoscope becomes more convenient.

SUMMARY OF THE INVENTION

Accordingly, it is a first object of the present invention to eliminate the above-described problems in the related art and to provide an all-pixels reading type electronic endoscope apparatus which can improve the picture quality by reading all the pixels, and which can recover the function of adjusting the quantity of light which becomes impossible of follow-up when a still picture is displayed.

It is a second object of the present invention to provide an all-pixels reading type electronic endoscope apparatus which can use the advantages of a function of adjusting the quantity of light and an electronic shutter function.

To achieve the first object, the present invention provides an all-pixels reading type electronic endoscope apparatus comprising: an all-pixels reading means for reading video signals on either of the odd lines and the even lines first and then reading the video signals on the other lines which are stored for each pixel by an image sensor at one exposure while cutting off the incident light for a predetermined period; all-pixels memories for storing the video signals on the odd lines and the video signals on the even lines obtained by the image sensor; a mixer for mixing the video signal on the odd lines and the video signals on the even lines which are read out of the all-pixels memories and forming pixel mixture signals; a light quantity controller for controlling the quantity of irradiated light on the basis of signals obtained by processing the pixel mixture signals output from the mixer; memories for a field picture for storing the video signals on the odd fields and the even fields formed on the basis of the pixel mixture signals; a freeze switch which is operated so as to form a still picture; and a control circuit for inhibiting the all-pixels memories from being written into at the point of time when the video signals on the odd lines and the even lines at the same exposure are stored in the all-pixels memories and forming a still picture when the freeze switch is operated, inhibiting the memories for a field picture from being written into and releasing the all-pixels memories from the write-inhibit state at the point of time when the video signals on the odd fields and the even fields at the same exposure are stored in the memories for a field picture, thereby quickly restoring the function of the light quantity controller which does not substantially work while the freeze button is operated.

According to the all-pixels reading type electronic endoscope apparatus, the electric charges are stored by the image sensor at a first exposure (exposure time is optional) within a first period of $1/60$ sec. (vertical synchronization period), the video signals on the odd lines, for example, are read out of transfer lines in a second period of $1/60$ sec., and the video signals on the even lines are read in a third period of $1/60$ sec. (next exposure). In order to read the video signals on the even lines, the light source is cut off by a cut-off means during the second period of $1/60$ sec. If the electric charges are stored at a next exposure during the second period when the video signals on the odd lines are read as in a conventional apparatus, it is impossible to read the video signal on the even lines. As a countermeasure, in the present invention, light is cut off during the second period, and the electric charges stored on the even lines are read during the third period. In this manner, it is possible to read all the signals for all the pixels obtained at one exposure.

After the video signal on the odd lines and the even lines are stored in the all pixel memories, all the video signals are read at the same time and mixed by the mixer. The pixel mixture signals are formed in the form of video signals as the odd field data and the even field data by the above-described color difference line-sequential pixel mixture signal reading method. These video signals are processed and stored in the memories for a field picture in the same way as in a conventional apparatus, and are finally output to a monitor or the like. In this manner, since a picture for one frame is formed on the basis of the signals for all the pixels obtained at one exposure during a period of $1/60$ sec., it is possible to produce a picture having a high picture quality.

When the freeze switch is operated so as to form a still picture, the all-pixels memories are inhibited from being written into at the point of time when the video signals on the odd lines and the even lines at the same exposure are stored in the all-pixels memories. On the other hand, at the point of time when the video signals on the odd fields and the even fields formed on the basis of the data in the all-pixels memories are stored in the memories for a field picture, the memories for a field picture are inhibited from being written into while the all-pixels memories is released from the write-inhibit state.

Consequently, a still picture is invariably composed of the video signals obtained at the same exposure within a period of $1/60$ sec., so that the picture of a high picture quality is obtained. In addition, since the video signals obtained at a next exposure are stored in the all-pixels memories before the freeze switch is turned off (before the still picture forming operation is cancelled). As a result, the light quantity controller is capable of controlling the quantity of light on the basis of the luminance signal or the like of the latest video signals, so that the follow-up brightness control based on the current state is quickly restored.

To achieve the second object, the present invention provides an all-pixels reading type electronic endoscope apparatus comprising: an all-pixels reading means; an all-pixels memories; a mixer; a light quantity controller for controlling the quantity of light output from a light source by operating a stop on the basis of a luminance signal of the video signals output from the mixer; an electronic shutter controller for controlling the storage time of the video signals in the image sensor as a shutter speed; and a main control circuit for controlling the shutter speed to a higher value when the stop of the light quantity controller is judged not to be in a full-open state, while controlling the shutter speed to a lower value when the stop is judged to be in a full-open state, and inhibiting the all-pixels memories from being written into at the point of time when the video signals on the odd lines and the even lines are stored therein so as to display a picture on the basis of the picture data at the same exposure.

According to this all-pixels reading type electronic endoscope apparatus, when the stop is not in a full-open state, in other words, when the endoscope is so close to the part as an object of observation that the quantity of light is sufficient, the shutter speed is made high, so that a sharp picture is obtained and the influence of the movement of the endoscope or the object of observation is small. Since a still picture is generally taken at a short distance, the shutter speed is made high, so that observation of a still picture having a high picture quality is enabled. On the other hand, when the stop is in a full-open state, the shutter speed is reduced, so that a sufficient quantity of light is available. For example, when the endoscope is directed toward the depth, it is possible to avoid the shortage of the quantity of light output from the light source.

In addition, since a picture for one frame is formed on the basis of the signals for all the pixels obtained at one exposure, the improvement of the picture quality owing to the electronic shutter function is made even remarkable. More specifically, even if the storage time for electronic charges is shortened due to the electronic shutter function, if a picture is formed on the basis of the signals obtained at two exposures as in a conventional endoscope, movement of the endoscope or the object of observation during the two exposures exerts deleterious influence on the picture quality. In contrast, in the present invention, since a still picture is formed on the video signals obtained at one exposure, the effect of shortening the storage time for electronic charges at one exposure is directly gained.

The above and other objects, features and advantages of the present invention will become clear from the following description of the preferred embodiments thereof, taken in conjunction with the accompanying drawings.

BRIEF DESCRIPTION OF THE DRAWINGS

FIG. 2 shows the picture data formed in the circuit between the CCD and the mixer in the embodiment shown in FIG. 1;

FIG. 9 is an explanatory view of the main operation of the second embodiment;

DESCRIPTION OF THE PREFERRED EMBODIMENTS

First Embodiment

Figure 1:
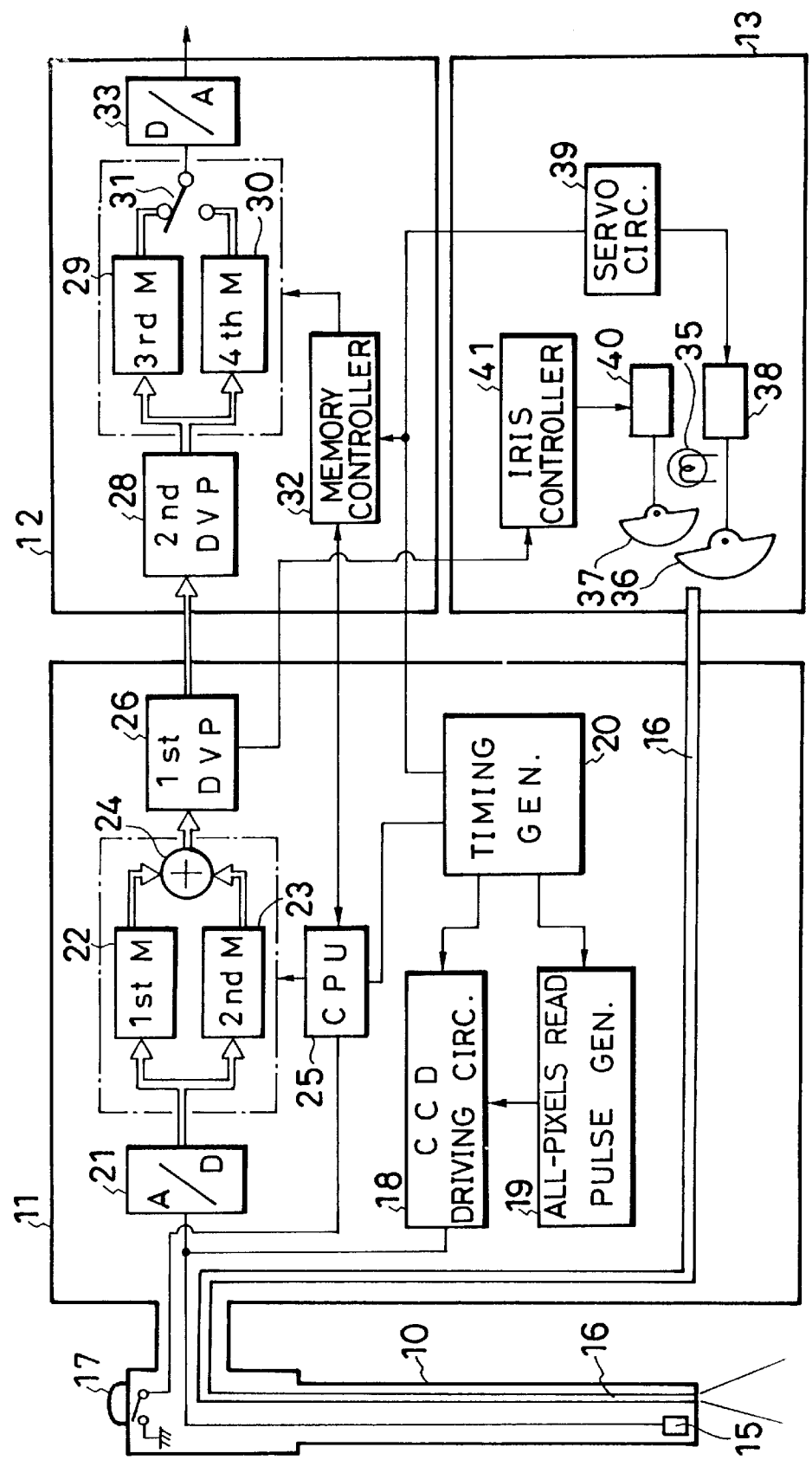
FIG. 1 is a block diagram of the circuit structure of a first embodiment of an all-pixels reading type electronic endoscope apparatus according to the present invention.
Figure 10A:
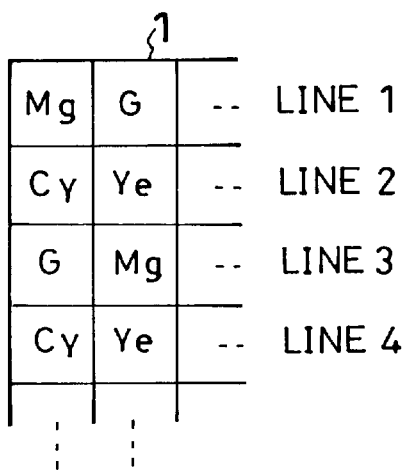
FIG. 10A shows the structure of color filters in a conventional CCD.
Figure 10B:
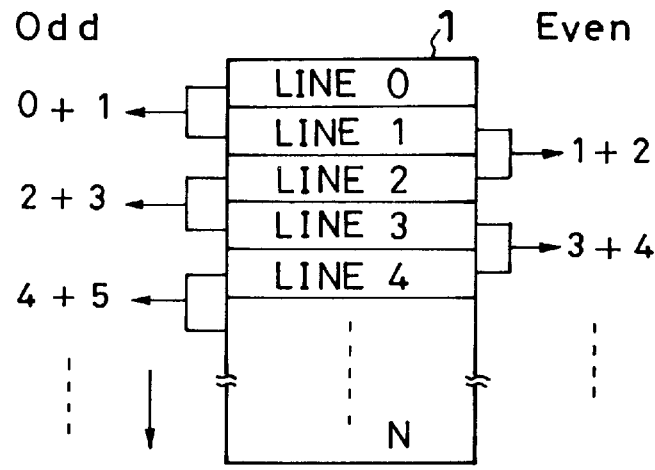
FIG. 10B is an explanatory view of the operation of reading pixel mixture signals from a conventional CCD.
Figure 11:
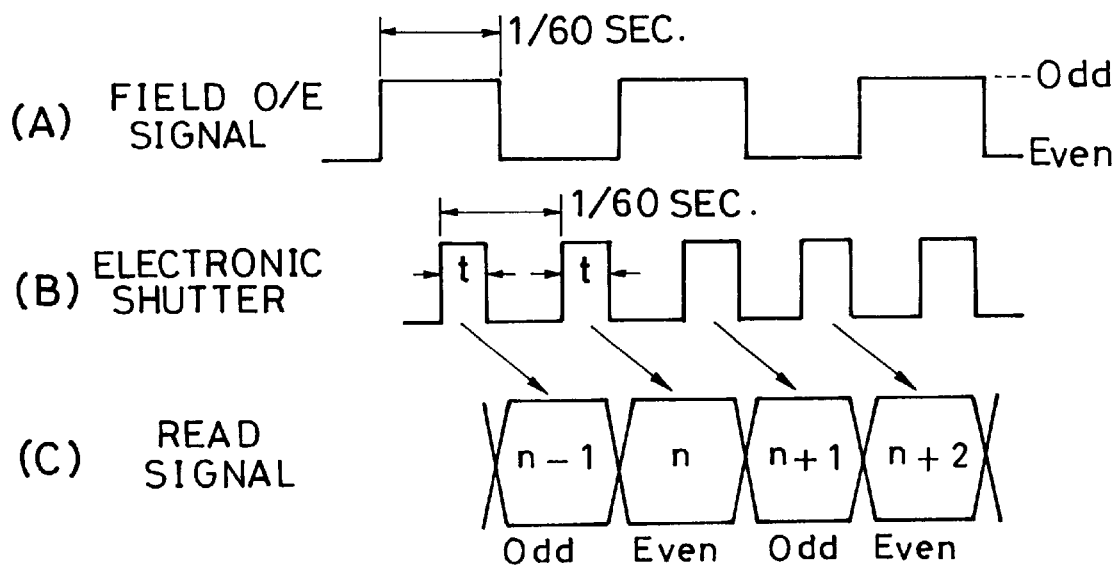
FIG. 11 is an explanatory view of the operation of a conventional CCD.

FIG. 1 shows the circuit structure of a first embodiment of an all-pixels reading type electronic endoscope apparatus according to the present invention. As shown in FIG. 1, the electronic endoscope apparatus is composed of an electronic endoscope 10 as a scope, a connector circuit 11 (internal circuit of the endoscope), a processor device 12 and a light source device 13. The electronic endoscope 10 is provided at the end portion with a CCD 15 which is provided with a mosaic color filter having a plurality colors similar to the one explained with reference to FIG. 10A, and a light guide 16 for introducing the light of the light source device 13 to the end portion. A freeze switch 17 which is operated so as to display a still picture is provided at the end of the handling portion of the electronic endoscope 10.

The connector circuit 11 is provided therein with a CCD driving circuit 18 for driving the CCD 15, an all-pixels read pulse generator 19 and a timing generator 20. The all-pixels read pulse generator 19 generates pulses for reading the data for all the pixels stored in the CCD 15 at one exposure, in two separate times for the data on the odd lined and the data on the even lines on the basis of the signals output from the timing generator 20. The CCD driving circuit 18 reads separately and sequentially the signals on the odd lines and the even lines from the CCD 15 on the basis of the read pulses.

The connector circuit 11 is also provided with an A/D converter 21 for inputting the output signals from the CCD 15, a first memory 22 (all-pixels memory) for storing the picture data on, for example, the odd lines, a second memory 23 (all-pixels memory) for storing the picture data on the even lines, a mixer 24, and a CPU 25 for controlling the entire operation including the operation of the memories 22, 23. The signals output from the CCD 15 are not output in the form of mixtures of signals on every two lines as in a conventional endoscope but the signals on the odd lines and the signals on the even lines are the temporarily stored in the respective memories 22, 23 separately from each other under the control of the CPU 25. Thereafter, the mixer 24 adds the data on the odd lines and the even lines so as to form signals similar to those formed by a conventional color difference line-sequential pixel mixture signal reading method.

FIG. 2 shows the picture data formed in the circuit between the CCD 15 and the mixer 24. The CCD 15 is provided with horizontal lines from line 0 to line N in correspondence with the number of scanning lines as shown in (A) and the picture data on the horizontal lines are transferred to transfer lines (not shown) and read. The data on the odd lines (lines 1, 3, 5 . . . ) in the CCD 15 are stored in the first memory 22 shown in (B), and the data on the even lines (lines 2, 4, 6 . . . ) are stored in the second memory 23 shown in (C).

The data stored in these memories 22, 23 are mixed by the mixer 24 so that the data on the same lines in (B) and (C) are added. As a result, the data on line 0+line 1, line 2+line 3, line 4+line 5, . . . are output as the Odd field data as shown in (D). Then the reading start line shown in (C) is shifted down by one line (the data are read from the position (C1)), and the data on the same lines in (B) and (C) are added. As a result, the data on line 1+line 2, line 3+line 4, line 5+line 6, . . . are output as the Even field data as shown in (E). The odd lines and the even line in the CCD 15 are referred to as ODD and EVEN, and the odd fields and the even fields as the object of interlaced scanning are referred to as Odd and Even, respectively.

In FIG. 1, a first DVP 26 (Digital Video Processor) is provided at a stage next to the mixer 24. The first DVP 26 processes the pixel mixture signals by the color difference line-sequential pixel mixture signal reading method so as to form, for example, a color difference signal and a luminance signal.

The processor device 12 to which the electronic endoscope 10 is connected is provided a second DVP 28 which is connected to the first DVP 26. The second DVP 28 is used for the control of the position of an image, the enlargement of an image, the formation of a mirror image, etc. At the stages next to the second DVP 28, there are provided a third memory 29 for storing the data on the Odd fields (memory for a field picture), a fourth memory 30 for storing the data on the Even fields (memory for a field picture), a switching circuit 31, a memory controller 32 and a D/A converter 33. The third memory 29 stores the data (D) in FIG. 2 on the Odd fields which are converted into a color difference signal and the like, and the fourth memory 30 stores the data (E) in FIG. 2 on the Even fields which are converted into a color difference signal and the like.

The memory controller 32 and the CPU 25 exerts the following controlling operation. When the freeze switch 17 is turned on, the all-pixels memories 22 and 23 are inhibited from being written into at the point of time when the video signals on the odd lines and the even lines at the same exposure are stored therein, and the video signals for the odd and even fields formed from these video signals are stored in the memories 29, 30 for a field picture. At the point of time when the video signals on the odd fields and the even fields at the same exposure are stored in the memories 29, 30 for a field picture, the memories 29, 30 are inhibited from being written into and the all-pixels memories 22, 23 are released from the write-inhibit state. Accordingly, the new picture data obtained by the CCD 15 are stored in the all-pixels memories 22 and 23 whether or not the freeze switch 17 is turned off.

A light source 35 is provided in the light source device 13 for connecting the light guide 16 disposed in the electronic endoscope 10, and a light chopper 36 and a stop 37 are disposed between the light source 35 and the incident end of the light guide 16. The light chopper 36 has a structure of rotating, for example, a semicircular disk, and is provided with a driving circuit 38 and a servo circuit 39 for rotating the light chopper 36 at a rate of one revolution in 1/30 sec. According to the light chopper 36, it is possible to output light for 1/60 sec. and cut off light for the next 1/60 sec in a field O/E signal which is output at intervals of 1/60 sec. The light chopper 36 therefore enables the data on the even lines to be read.

A driving circuit 40 and an iris controller 41 are connected to the stop 37. The driving circuit 40 and the iris controller 41 drive the stop 37 so as to adjust the quantity of output light on the basis of the luminance signal obtained from the first DVP 26. Since the all-pixels memories 22, 23 are released from the write-inhibit state during the operation of a still picture even if the freeze switch 17 is not turned off, as described above, the iris controller 41 controls the quantity of output light on the basis of the luminance signal obtained from the current video signals even while the still picture is displayed.

The operation of the embodiment having the above-described structure will now be explained with reference to FIGS. 3 and 4. In FIG. 4, a timing signal which forms one field in 1/60 sec. is used as a field O(Odd)/E(Even) signal (A) in the same way as in a conventional apparatus. In correspondence with this signal, the light chopper 36 ready for use is rotated at a rate of one revolution in 1/30 sec. In this manner, light is alternately output and cut off for 1/60 sec, as indicated with Pn–1, Pn, Pn+1, . . . in (B) of FIG. 4. The light is irradiated into the body of observation from the end portion through the light guide 16.

Under the irradiated light, the CCD 15 at the end portion catches the image within the body of observation and electric charges corresponding to the image are stored in the CCD 15. The CCD driving circuit 18 reads the stored electric charges in accordance with the pulses input from the all-pixels read pulse generator 19, and the data for all the pixels stored in the CCD 15 at one exposure are read.

To state this more concretely, at the exposure to the output light Pn–1 in (B) of FIG. 4, the data on (n–1) ODD lines and the data on (n–1) EVEN lines are sequentially read out of the CCD 15, as shown in (C) of FIG. 4. The data on the ODD lines are stored in the first memory 22 in accordance with the write enable signal (E) in FIG. 4, while the data on the EVEN lines are stored in the second memory 23 in accordance with the write enable signal (F) in FIG. 4. Similarly, when the light Pn, Pn+1 . . . is output, the data on the ODD lines and the EVEN lines are read and stored in the respective memories 22, 23.

The data in the all-pixels memory 22, 23 are mixed by the mixer 24, and, for example, an Odd field signal obtained by mixing the data on an ODD line and the data on an EVEN line in the (n–2)th output, an Even field signal obtained by mixing the data on an EVEN line in the (n–2)th output and the data on an ODD line in the (n–1)th output, an ODD field signal obtained by mixing the data on an ODD line and the data on an EVEN line in the (n–1)th output, . . . are sequentially formed, as shown in (G) of FIG. 4. These field signals are subjected to color image processing, and temporarily stored in the third memory 29 and the fourth memory 30. The outputs of these memories 29 and 30 are alternately output to the monitor by the switching circuit 31 and a picture is displayed by interlaced scanning.

In this manner, when a moving picture is displayed in this embodiment, a part of the picture data obtained by the next exposure are mixed therewith. However, since the amount of data mixed therewith is ½ of all the data, even if the endoscope 10 or the object of observation moves during the period of 1/60 sec, the influence is small.

In addition, as to the electronic shutter function, since a picture is formed at one exposure, the effect of shortening the shutter speed (storage time) within a period of 1/60 sec. is directly manifested and it is possible to improve the picture quality in a bright state or the like by the short storage time of the CCD 15.

Figure 3:
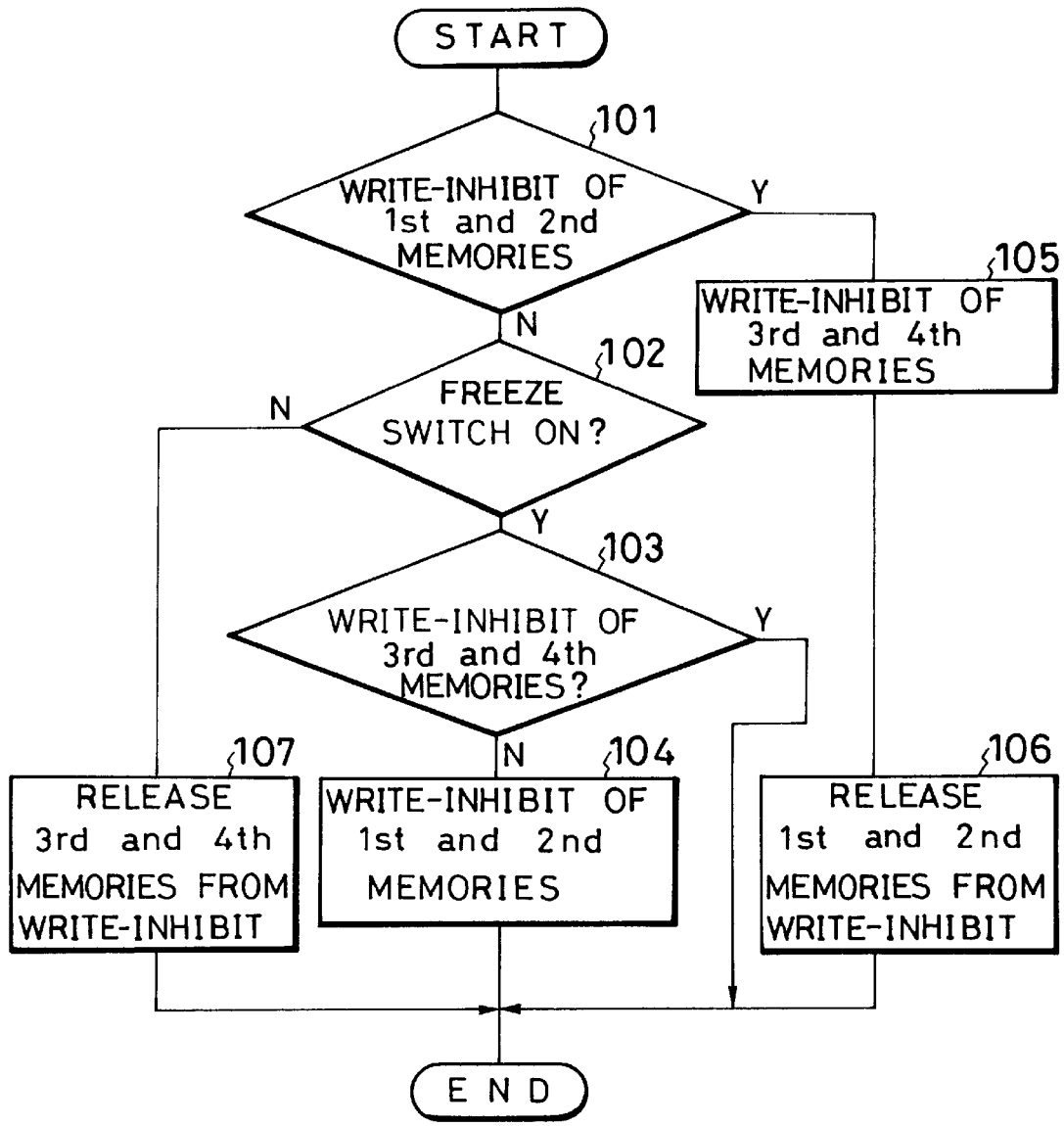
FIG. 3 is a flow chart of the controlling operation in the all-pixels memories and the memories for a field picture in the first embodiment.
Figure 4:
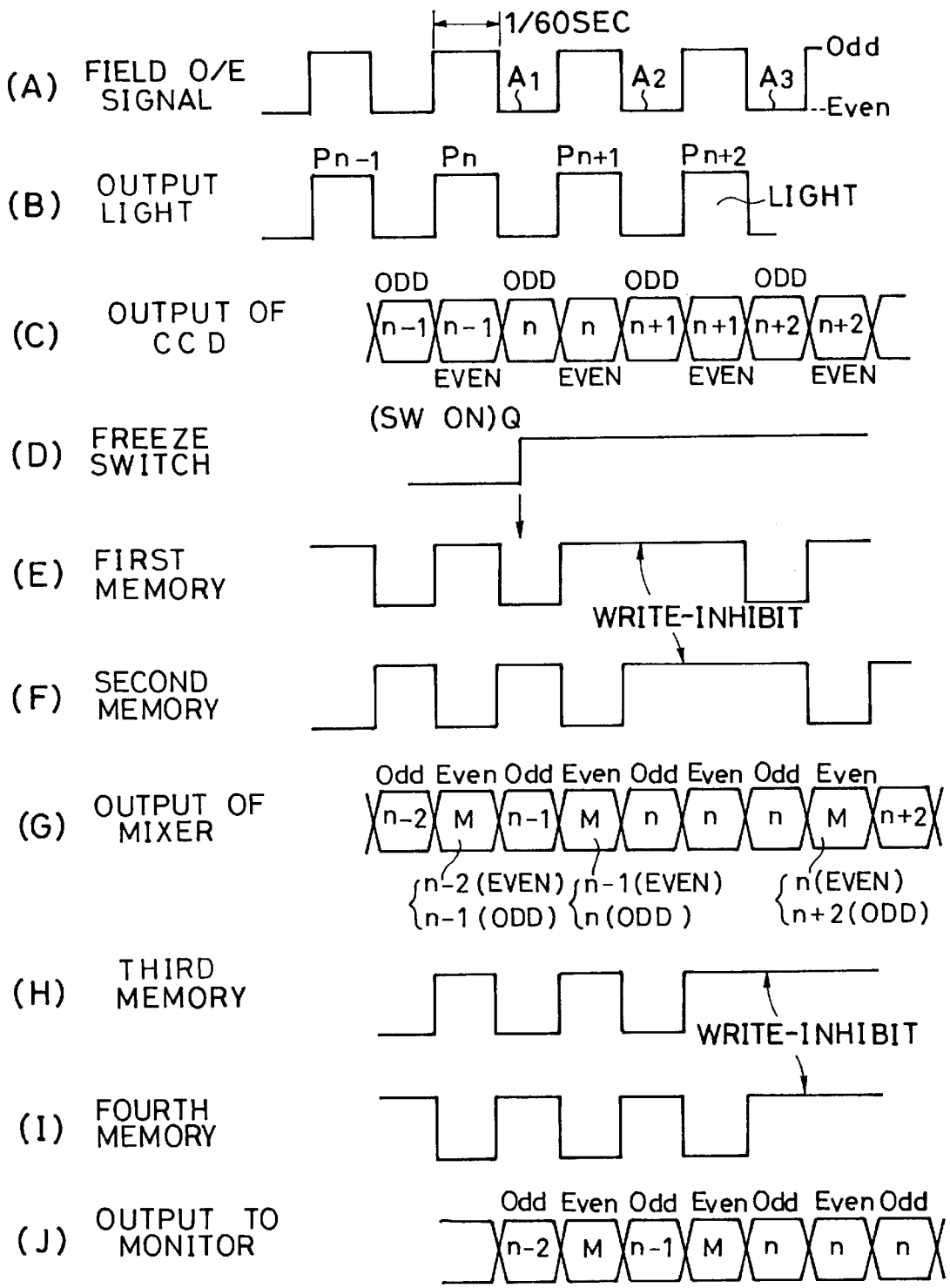
FIG. 4 is an explanatory view of the main operation of the first embodiment.

FIG. 3 shows the controlling operation in each memory during the formation of a still picture. Under the control of the CPU 25 and the memory controller 32 shown in FIG. 1, a still picture is displayed by using only the data stored at the same exposure and the light quantity control in conformity with the current state is quickly restored. Each operation is so set as to be executed at the fall of the O/E signal (A). At step 101 (FIG. 3), whether or not the first memory 22 and the second memory 23 are inhibited from being written into is detected, and at step 102, whether or not the freeze switch 17 is pressed down (ON) is detected. If the freeze switch 17 is ON, whether or not the third memory 29 and the fourth memory 30 are inhibited from being written into is detected at step 103.

At step 104, the first memory 22 and the second memory 23 are inhibited from being written into. For example, if the freeze switch 17 is turned on at the point Q in (D) of FIG. 4, which is at a fall (A1) of the field O/E signal, each of the memories 22, 23 is inhibited from being written into at the next fall (A2), as shown in (E) and (F) of FIG. 4. Therefore, no data is written in the state in which the data on n odd lines obtained at the exposure to the output light Pn are written in the first memory 22 and the data on n even lines are written in the second memory 23.

As a result, Odd field signals obtained by mixing the data on the odd lines in the n-th output and Even field signals obtained by mixing the data on the even lines in the n-th output are alternately read, as shown in (G) of FIG. 4, and after these field signals are subjected to various signal processings, they are stored in the third memory 29 and the fourth memory 30.

In this case, at the step 101, since it is judged that the first memory 22 and the second memory 23 are in a write-inhibt state at the fall (A2), the process proceeds to step 105 and the third memory 29 and the fourth memory 30 are inhibited from being written into, as shown in (H) and (I) of FIG. 4. At the same time, the first memory 22 and the second memory 23 are released from the write-inhibit state at step 106. This operation is executed at the next fall (A3).

According to this operation, the odd field signals and the Even field signals in the n-th output which are read out of the third memory 29 and the fourth memory 30 are output to the monitor, as shown in (J) of FIG. 4 and a still picture is displayed by interlaced scanning. Since a still picture is displayed on the basis of the data on all the pixels at the same exposure, it is possible to produce the image of the object of observation having a high picture quality.

Even during the display of the still picture, the first memory 22 and the second memory 23 are released from the write-inhibit state, as described above, and newly obtained video signals are stored in the CCD 15. The current luminance signal is therefore supplied from the first DVP 26 to the iris controller 41, and the iris controller 41 controls the stop 37 on the basis of the current luminance signal, so that the optimum light is output in accordance with the current state. Consequently, it is possible to prevent halation from being caused, the screen from becoming dark or the diseased part from being burdened when the operation of the still picture is cancelled by turning off the freeze switch 17.

When the freeze switch 17 is turned off, the process proceeds from the step 102 to step 107 in FIG. 3, and the third memory 29 and the fourth memory 30 are released from the write-inhibit state, thereby changing the still picture over to a moving picture.

As explained above, according to the first embodiment, the picture quality is improved by reading all the pixels, and accurate information for the control of the quantity of light is obtained from the current picture data. Accordingly, it is possible to quickly restore the function of controlling the quantity of light which becomes impossible of follow-up when a still picture is displayed. Thus, a moving picture is obtained with an appropriate quantity of light, and the burden on the diseased part is lightened.

Second Embodiment

Figure 5:
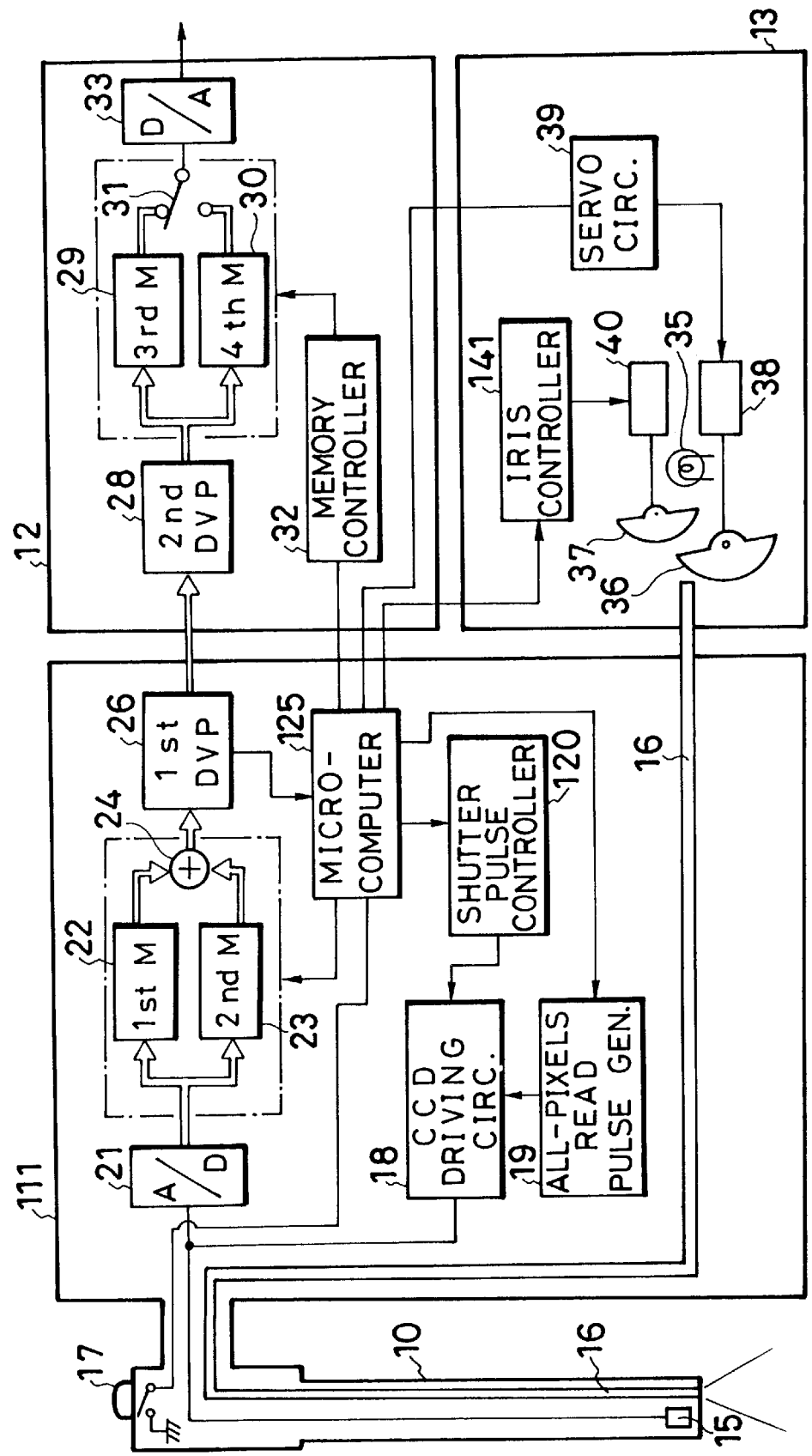
FIG. 5 is a block diagram of the circuit structure of a second embodiment of an all-pixels reading type electronic endoscope apparatus according to the present invention.

FIG. 5 shows the circuit structure of a second embodiment of an all-pixels reading type electronic endoscope apparatus provided with an electronic shutter function according to the present invention. The fundamental structure of the electronic endoscope 10, a connector circuit 111, the processor device 12 and the light source device 13 are the same as that of the first embodiment. The all-pixels read pulse generator 19 generates pulses for reading the data for all the pixels stored in the CCD 15 at one exposure, in two separate times for the data on the odd lined and the data on the even lines. The CCD driving circuit 18 reads separately and sequentially the signals on the odd lined and the even lines from the CCD 15 on the basis of the read pulses. The connector circuit 111 is also provided with a shutter pulse controller 120. The shutter pulse controller 120 forms shutter pulses for determining the shutter speed in the electronic shutter function. It is possible to set the shutter speed between, for example, $\frac{1}{60}$ sec and $\frac{1}{400}$ sec by varying the timing of the shutter pulses.

The A/D converter 21 is provided with the first memory 22, the second memory 23, the mixer 24 and a microcomputer 125 for controlling the entire operation including the operation of the memories 22, 23. The video signals on the odd lines and the video signal on the even lines output from the CCD 15 are temporarily stored in the respective memories 22, 23 separately from each other under the control of the microcomputer 125. Thereafter, the mixer 24 adds the data on the odd lines and the even lines and executes the processing explained in the first embodiment with reference to FIG. 2 so as to form signals similar to those formed by a conventional color difference line-sequential pixel mixture signal reading method.

The processor device 12 is provided the second DVP 28, the third memory 29, the fourth memory 30, the switching circuit 31, the memory controller 32 and the D/A converter 33.

The light source device 13 is provided in the light source 35, the light chopper 36 and the stop 37. According to the light chopper 36, it is possible to output light for $\frac{1}{60}$ sec. and cut off light for the next $\frac{1}{60}$ sec in a field O/E signal which is output at intervals of $\frac{1}{60}$ sec. The light chopper 36 therefore enables the data on the even lines to be read.

The driving circuit 40 and an iris controller 141 are connected to the stop 37. The driving circuit 40 and the iris controller 141 drive the stop 37 in accordance with a control signal from the microcomputer 125. The luminance signal obtained from the first DVP 26 is supplied to the microcomputer 125, and the iris controller 141 supplies a control signal which adjusts the luminance signal to a predetermined value to the driving circuit 40 under the control of the microcomputer 125. Thus, the quantity of light output from the light source 35 is adjusted.

The microcomputer 125 also controls the shutter pulse controller 120 so as to vary the electronic shutter speed on the basis of the state of the stop 37 which is controlled in accordance with the luminance signal.

Figure 6:
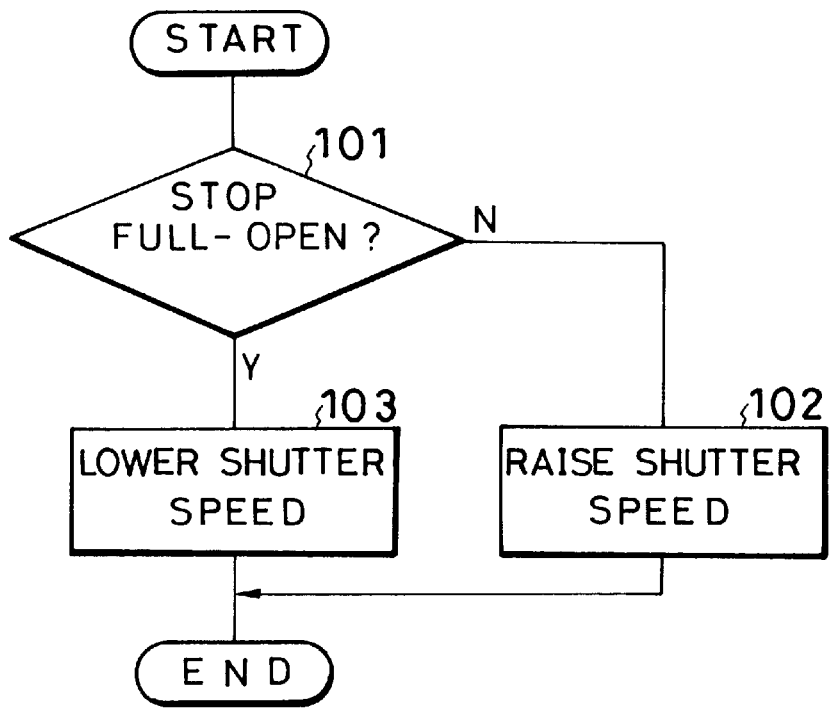
FIG. 6 is a flow chart of the electronic shutter function controlling operation of the microcomputer in the embodiment shown in FIG. 5.

FIG. 6 shows the electronic shutter controlling operation of the microcomputer 125. The controlling operation is executed at intervals of a predetermined time such as 16.6 ms. At step 101, whether or not the stop 37 is in a full-open state is first judged. If the answer is in the negative, the process proceeds to step 102 and the electronic shutter speed is raised. That is, when the stop 37 is not in a full-open state, the end portion of the endoscope 10 is close to the object of observation and adequate light is irradiated, so that the shutter pulse controller 20 outputs a shutter pulse which produces a higher shutter speed. For example, if the image is being taken at a shutter speed of $\frac{1}{60}$ sec, as shown in FIG. 7, the shutter speed is changed over to a higher speed toward $\frac{1}{200}$ sec.

On the other hand, if the stop 37 is judged to be in a full-open state at the step 101, the process proceeds to step 103 and the electronic shutter speed is lowered. For example, if the image is being taken at a shutter speed of $\frac{1}{400}$ sec, as shown in FIG. 8, the shutter pulse controller 20 forms a shutter pulse which changes over the shutter speed to a lower speed toward $\frac{1}{200}$ sec.

Figure 7:
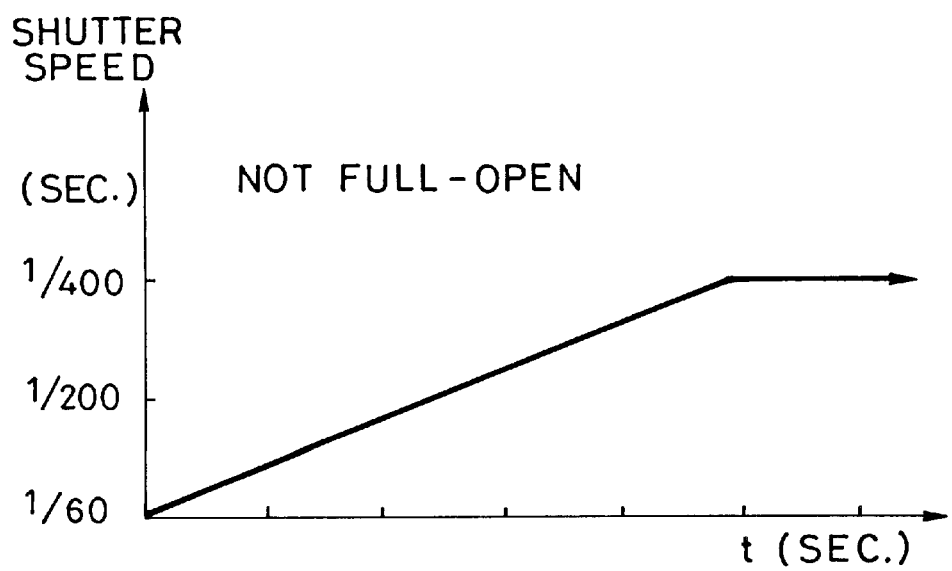
FIG. 7 shows a graph of the shutter speed set when the state in which the stop is not in a full-open state continues in the second embodiment.
Figure 8:
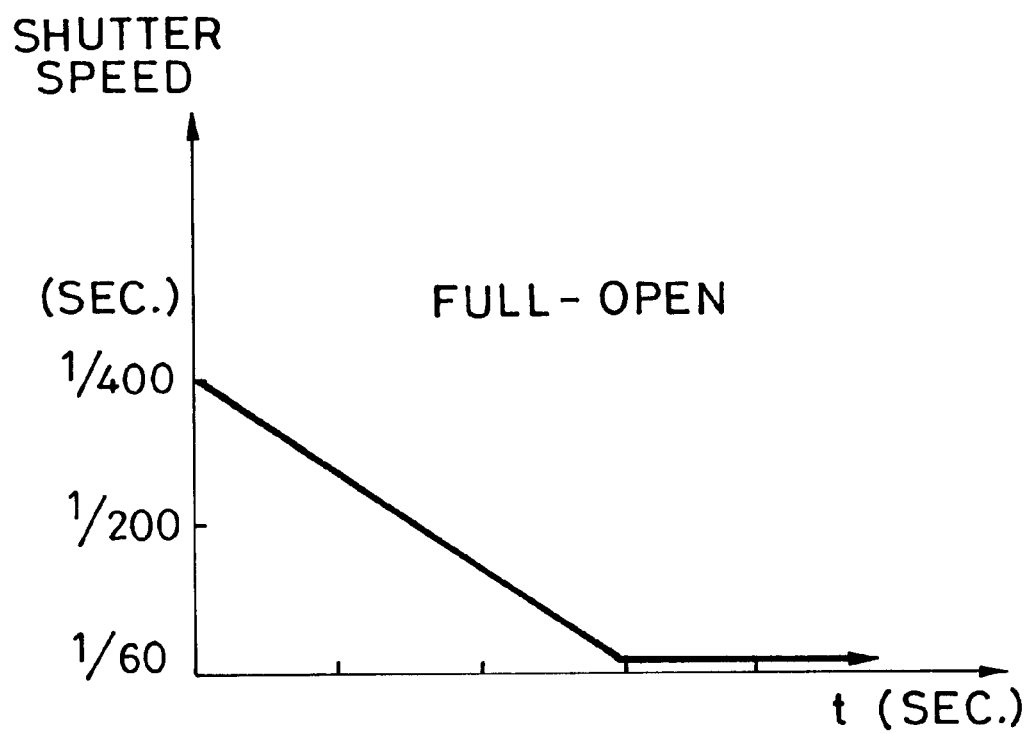
FIG. 8 shows a graph of the shutter speed set when the state in which the stop is in a full-open state continues in the second embodiment.

It is possible to set the shutter speed shown in FIGS. 7 and 8 roughly at, for example, $\frac{1}{60}$ sec., $\frac{1}{200}$ sec. and $\frac{1}{400}$ sec.

The operation of the second embodiment having the above-described structure will now be explained with reference to FIG. 9. A timing signal which forms one field in $\frac{1}{60}$ sec. is used as a field O(Odd)/E(Even) signal (A) in the same way as in a conventional apparatus. In correspondence with this signal, the light chopper 36 ready for use is rotated at a rate of one revolution in $\frac{1}{30}$ sec. In this manner, light is alternately output and cut off for $\frac{1}{60}$ sec, as indicated with Pn-1, Pn, Pn+1, . . . in (B) of FIG. 9. The light is irradiated into the body of observation from the end portion through the light guide 16.

Under the irradiated light, the CCD 15 at the end portion catches the image within the body of observation and electric charges corresponding to the image are stored in the CCD 15 at a shutter speed (t) set within $\frac{1}{60}$ sec, as will be described later. The CCD driving circuit 18 reads the stored electric charges in accordance with the pulses input from the all-pixels read pulse generator 19, and the data for all the pixels stored in the CCD 15 at one exposure are read.

To state this more concretely, at the exposure to the output light Pn-1 in (B) in FIG. 9, the data on (n-1) ODD lines and the data on (n-1) EVEN lines are sequentially read out of the CCD 15, as shown in (D) of FIG. 9. The data on the ODD lines are stored in the first memory 22 in accordance with the write enable signal (F) of FIG. 9, while the data on the EVEN lines are stored in the second memory 23 in accordance with the write enable signal (G) in FIG. 4. Similarly, when the light Pn, Pn+1 . . . is output the data on the ODD lines and the EVEN lines are read and stored in the respective memories 22, 23.

The data in the all-pixels memory 22, 23 are mixed by the mixer 24, and, for example, an Odd field signal obtained by mixing the data on an ODD line and the data on an EVEN line in the (n−2)th output, an Even field signal obtained by mixing the data on an EVEN line in the (n−2)th output and the data on an ODD line in the (n−1)th output, an ODD field signal obtained by mixing the data on an ODD line and the data on an EVEN line in the (n−1)th output, . . . are sequentially formed, as shown in (H) of FIG. 9. These field signals are subjected to color image processing, and temporarily stored in the third memory 29 and the fourth memory 30. The outputs of these memories 29 and 30 are alternately output to the monitor by the switching circuit 31 and a picture is displayed by interlaced scanning.

In this manner, when a moving picture is displayed in this embodiment, a part of the picture data obtained by the next exposure are mixed therewith. However, since the amount of data mixed therewith is ½ of all the data, even if the endoscope 10 or the object of observation moves during the period of 1/60 sec, the influence is small.

During the formation of such a picture, the shutter speed is controlled in accordance with the state of the stop 37. As explained in FIG. 6, whether or not the stop 37 is in a full-open state is judged. If the stop 37 is not in a full-open state, that is, if the end portion of the endoscope 10 is close to the part as the object of observation and light is efficiently irradiated, the shutter speed is raised. In other words, the shutter pulse controller 20 outputs a shutter pulse which shortens the storage time. For example, if the shutter speed (t) is 1/60 sec in FIG. 7, and the stop 37 is not in a full-open state, the shutter speed is changed over to 1/200 sec. Even if the stop 37 is not in a full-open state at a shutter speed of 1/200 sec, the shutter speed is further raised to 1/400 sec.

In this embodiment, the maximum shutter speed is set at 1/400 sec, but it may be set at any other value. In this embodiment, the maximum shutter speed is set a a comparatively low value so that, for example, when a still picture is formed at a short distance, the maximum shutter speed of 1/400 sec. may be obtained before the stop 37 does not reach the full-open value.

When the end portion of the endoscope 10 is not close to the part as the object of observation and the stop 37 is not in a full-open state, the shutter speed is lowered. For example, if the shutter speed (t) is 1/400 sec in FIG. 8, it is changed over to 1/200 sec. Even if the stop 37 maintains a full-open state at a shutter speed of 1/200 sec, the shutter speed is further lowered to 1/60 sec. When the endoscope 10 is directed toward the depth, the stop 37 often maintains a full-open state even at a shutter speed of 1/60 sec. However, the shutter speed of 1/60 sec is enough to take a peripheral part necessary for the observation.

According to this light quantity control and the electronic shutter control based on the state of the stop 37, it is possible to use a high shutter speed and obtain a picture having a sharp and high picture quality at a take at a short distance (still picture or the like). On the other hand, if the distance between the end portion of the endoscope 10 and the object of observation is not short, adequate quantity of light is obtained. In addition, in an electronic endoscope adopting all-pixels reading system as the present invention, since it is possible to form a picture at one exposure, the effect of shortening the shutter speed (storage time) is directly manifested and it is possible to improve the picture quality at a take at a short distance by the short shortage time of the CCD 15.

On the other hand, a still picture is displayed by using only the data obtained at the same exposure. Under the control of the microcomputer 125, the first memory 22 and the second memory 23 are inhibited from being written into during the formation of a still picture in the same way as in the first embodiment. For example, if the freeze switch 17 is turned on at the point Q in (E) of FIG. 9, each of the memories 22, 23 is inhibited from being written into at the next fall (A2), as shown in (F) and (G) of FIG. 9. Therefore, no data is written in the state in which the data on n odd lines obtained at the exposure to the output light Pn are written in the first memory 22 and the data on n even lines are written in the second memory 23.

As a result, Odd field signals obtained by mixing the data on the odd lines in the n-th output and Even field signals obtained by mixing the data on the even lines in the n-th output are alternately read, as shown in (H) of FIG. 9, and after these field signals are subjected to various signal processings, they are stored in the third memory 29 and the fourth memory 30.

In this manner, a combination of field pictures at different exposures is inhibited, and a still picture is displayed on the basis of the data on all the pixels at the same exposure. It is therefore possible to produce the image of the object of observation having a high picture quality. In addition, the use of the above-described electronic shutter function enables a further improvement of the picture quality.

As explained above, according to the second embodiment, it is possible to use the advantages of the electronic shutter function for producing a high quality even if there is movement in the endoscope or the object of observation and the light quantity control function for varying the intensity of the output light itself.

While there has been described what are at present considered to be preferred embodiments of the invention, it will be understood that various modifications may be made thereto, and it is intended that the appended claims cover all such modifications as fall within the true spirit and scope of the invention.

What is claimed is:

1. An all-pixels reading type electronic endoscope apparatus comprising:

an all-pixels reading means for reading video signals on either of the odd lines and the even lines first and then reading the video signals on the other lines which are stored for each pixel by an image sensor at one exposure while cutting off incident light for a predetermined period;

all-pixels memories for storing said video signals on said odd lines and said video signals on said even lines obtained by said image sensor;

a mixer for mixing said video signals on said odd lines and said videos signals on said even lines which are read out of said all-pixels memories and forming pixel mixture signals;

a light quantity controller for controlling the quantity of irradiated light on the basis of signals obtained by processing said pixel mixture signals output from said mixer;

memories for a field picture for storing said video signals on odd fields and even fields formed on the basis of said pixel mixture signals;

a freeze switch which is operated so as to form a still picture; and a control circuit for inhibiting said all-pixels memories from being written into at the point of time when said video signals on said odd lines and said even lines at the same exposure are stored in said all-pixels memories and forming a still picture when said freeze switch is operated, inhibiting said memories for a field picture from being written into and releasing said all-pixels memories from the write-inhibit state at the point of time when said video signals on said odd fields and said even fields at the same exposure are stored in said memories for a field picture, thereby quickly restoring the function of said light quantity controller which does not substantially work while said freeze button is operated.

* * * * *